(12) United States Patent
Tanoshima et al.

(10) Patent No.: US 8,961,876 B2
(45) Date of Patent: Feb. 24, 2015

(54) SAMPLE ANALYZER

(75) Inventors: Eiji Tanoshima, Kobe (JP); Naohiko Matsuo, Kobe (JP); Eiji Hama, Shiojiri (JP)

(73) Assignee: Sysmex Corporation, Kobe-Shi, Hyogo (JP)

( * ) Notice: Subject to any disclaimer, the term of this patent is extended or adjusted under 35 U.S.C. 154(b) by 48 days.

(21) Appl. No.: 13/302,343

(22) Filed: Nov. 22, 2011

(65) Prior Publication Data

US 2012/0129247 A1    May 24, 2012

(30) Foreign Application Priority Data

Nov. 24, 2010 (JP) .................................. 2010-261694

(51) Int. Cl.
*G06F 19/00* (2011.01)
*G01N 35/00* (2006.01)

(52) U.S. Cl.
CPC .. *G01N 35/00732* (2013.01); *G01N 2035/0091* (2013.01); *G01N 2035/00891* (2013.01); *G01N 35/00663* (2013.01); *G01N 35/00871* (2013.01); *G01N 2035/00752* (2013.01)
USPC .................. 422/67; 422/63; 700/266; 702/84

(58) Field of Classification Search
CPC .............. G01N 2035/00752; G01N 35/00732; G01N 2035/00891; G01N 2035/0091
See application file for complete search history.

(56) References Cited

U.S. PATENT DOCUMENTS

2010/0111767 A1 * 5/2010 Yonekura et al. ................ 422/65
2013/0018618 A1 * 1/2013 Eshima et al. .................. 702/83

FOREIGN PATENT DOCUMENTS

JP    2008-096214 A    4/2008

OTHER PUBLICATIONS

Diagnostic Test Group, Clarity Urocheck 120 Urine analyzer Instruction Manual, pp. 1-20, effective date Jan. 18, 2010, www.claritydiagnostics.com/files/inserts/DTG-UAM%20Manual.pdf.*

* cited by examiner

*Primary Examiner* — P. Kathryn Wright
(74) *Attorney, Agent, or Firm* — Brinks Gilson & Lione (57) ABSTRACT

A sample analyzer for analyzing a sample with a liquid in a container is disclosed. The sample analyzer comprises: a reader that reads an information of a liquid in a container, the information of the liquid being stored in a storage medium; a display; and a controller including a processor and a memory under control of the processor, the memory storing instruction causing the processor to carry out operations comprising: determining whether the sample analyzer is ready to read the information of the liquid by the reader; and causing, when the sample analyzer is determined to be ready, the display to display an indication that indicates the sample analyzer is ready to read the information of the liquid by the reader.

16 Claims, 13 Drawing Sheets

| Calibration Curve | | | | |
|---|---|---|---|---|
| PT% | sec | PT | Date Set | Lot. No. | Expiration Date |
| 100.0 | 0.0 | | | | |
| 50.0 | 0.0 | | | | |
| 25.0 | 0.0 | | | | |
| 12.5 | 0.0 | | | | |
| 6.3 | 0.0 | | | | |
| 3.1 | 0.0 | | | | |

STANDBY — Rack Replaceable
HC IP
PT
Date Set 2009/11/10

Normal Value: 0.0
ISI: 0.00

Reagent 1

Reference   Exit 300, 31, 32, 33

| Calibration curve | | | | |
|---|---|---|---|---|
| PT% | sec | PT | Setting date 2009/11/10 | |
| % | | | Lot. No. | Expiration date |
| 100.0 | 0.0 | | 526932 | 2010/12/31 |
| 50.0 | 0.0 | | | |
| 25.0 | 0.0 | | | |
| 12.5 | 0.0 | Reference | | |
| 6.3 | 0.0 | | | |
| 3.1 | 0.0 | | | |
| Normal value | 0.0 | | | |
| ISI | 0.00 | | | |

Standby
Rack replaceable

HC IP
PT
(M)

Reagent 1

Reference  Exit

FIG. 13

SAMPLE ANALYZER

RELATED APPLICATIONS

This application claims priority under 35 U.S.C. §119 to Japanese Patent Application No. 2010-261694 filed on Nov. 24, 2010, the entire content of which is hereby incorporated by reference.

BACKGROUND OF THE INVENTION

1. Field of the Invention

The present invention relates to a sample analyzer for analyzing a samples using liquids such as reagents, controls, calibrators and the like.

2. Description of the Related Art

Many conventional sample analyzers have been developed for analyzing samples using liquids such as reagents, controls, calibrators and the like. For example, Japanese Laid-Open Patent Publication No. 2008-096214 discloses an automatic analyzer provided with a barcode reader for obtaining reagent information from a barcode affixed to the reagent container that contains the reagent. The automatic analyzer obtains the reagent information relating to the reagent when the user scans the barcode affixed to the reagent container using the barcode reader.

The conventional sample analyzer disclosed in Japanese Laid-Open Patent Publication No. 2008-096214 requires that the user manually scans the barcode. However, a user who is unfamiliar with the operation of the apparatus may have difficulty in determining whether the reagent information has been satisfactorily read by the automatic analyzer via the arbitrary timing used to scan the barcode.

SUMMARY OF THE INVENTION

A first aspect of the present invention is a sample analyzer for analyzing a sample with a liquid in a container. The sample analyzer comprises: a reader that reads an information of a liquid in a container, the information of the liquid being stored in a storage medium; a display; and a controller including a processor and a memory under control of the processor, the memory storing instruction causing the processor to carry out operations comprising: determining whether the sample analyzer is ready to read the information of the liquid by the reader; and causing, when the sample analyzer is determined to be ready, the display to display an indication that indicates the sample analyzer is ready to read the information of the liquid by the reader.

DETAILED DESCRIPTION OF THE PREFERRED EMBODIMENTS

Figure 1:
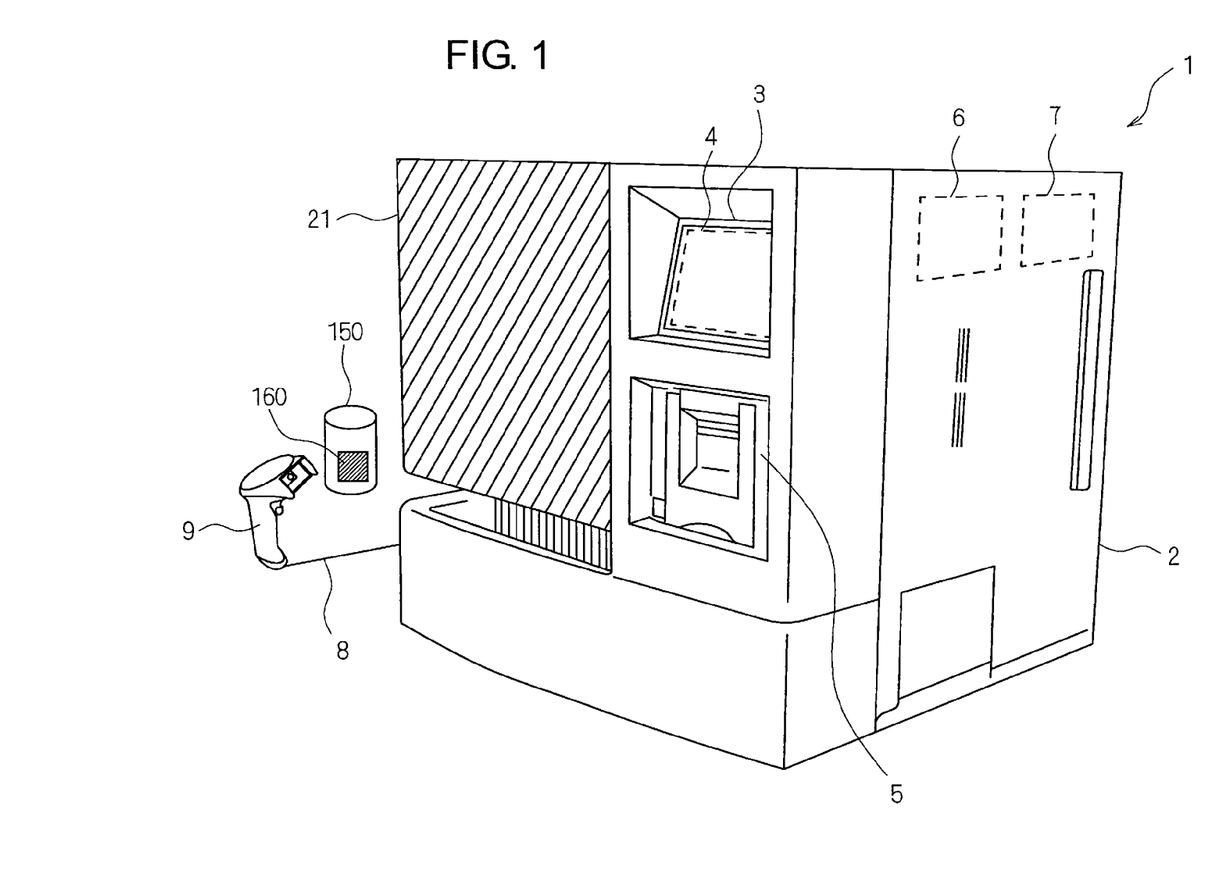
FIG. 1 is a perspective view schematically showing the structure of an embodiment of the sample analyzer of the present invention.

The present embodiment of the sample analyzer is described, based on the drawing, in terms of a blood coagulation measuring apparatus for analyzing the coagulation factor activity in blood samples. The present embodiment is described in terms of a sample analyzer 1 (refer to FIG. 1) for analyzing samples using reagent accommodated in reagent containers 150 (refer to FIG. 1) as the liquid accommodated in liquid containers. In the present embodiment, the reagent container 150 has an attached recording medium which records information related to the reagent accommodated in the reagent container 150 as the liquid information related to the liquid accommodated in the liquid container. The recording medium in the present embodiment is a two-dimensional code 160 (refer to FIG. 1). The information related to the reagent includes the reagent lot number and expiration date (this information, in aggregate, is referred to generically as reagent information hereinafter) in the present embodiment. Note that the sample analyzer 1 is not limited to blood coagulation measuring apparatuses, and ALSO may be, for example, a clinical sample analyzer such as a hemocytometer, immunoanalyzer, biochemical analyzer, urine analyzer, or an industrial particle measuring apparatus, FIG. 1 is a perspective view schematically showing the structure of an embodiment of the sample analyzer 1 of the present invention. As shown in FIG. 1, the housing 2 of the sample analyzer 1 of the present embodiment has a cover 21 which opens and closes over a concavity on the upper part of the front left side. A display 3, such as a liquid crystal panel or the like, is provided above the front right side of the housing 2.

The display 3 is a touch panel-type display provided with a touch panel 4 on the front surface. Provided within the housing 2 are a control unit 6 for controlling the operations of the various hardware of the sample analyzer 1, and a communication part 7 for data communication with an external computer, various devices and the like. The sample analyzer 1 has a hand-held reader 9 for obtaining reagent information recorded on the two-dimensional code 160 affixed to the reagent container 150. The hand-held reader 9 is connected via a connection line 8 so as to be capable of data communication with the control unit 6.

Figure 2:
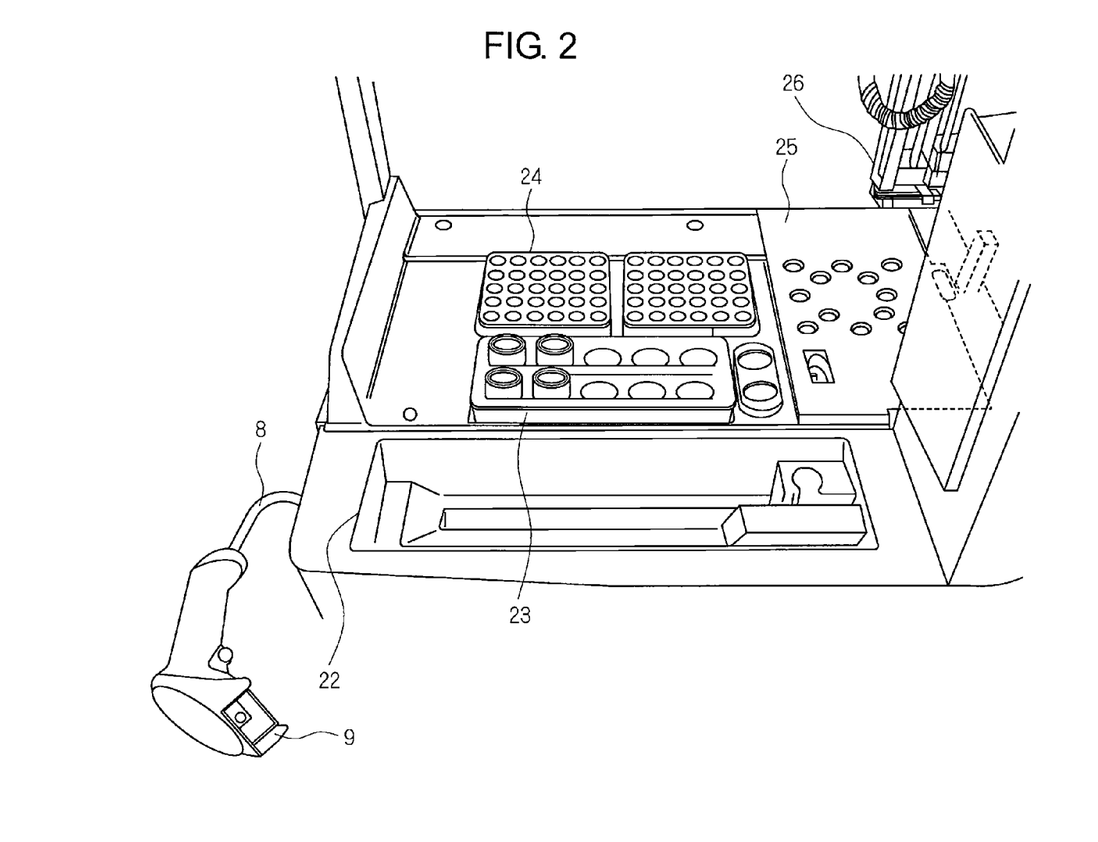
FIG. 2 is a partial enlargement perspective view showing the open cover of the embodiment of the sample analyzer of the present invention.

FIG. 2 is a partial enlargement perspective view showing the open cover 21 of the embodiment of the sample analyzer 1 of the present invention. As shown in FIG. 2, a sample container holder 22 for loading a sample container accommodating a sample is provided at a concavity on the front side of the housing 2 covered by the cover 21. The user can load a sample rack holding a plurality of sample containers into the sample container holder 22. The sample analyzer 1 performs measurements on the sample accommodated in the sample container.

A reagent holder 23 is provided on the inner side of the sample container holder 22. The reagent rack, which holds a plurality of reagent containers 150 accommodating reagent, is loaded in the reagent holder 23. On the inner side of the reagent holder 23 is provided a cuvette holder 24 for holding a plurality of cuvettes (transparent reactor containers) used in measurements.

A measuring unit 25 which performs sample measurements is disposed on the right side of the cuvette holder 24, and a sample and reagent dispenser 26 is provided above the sample container holder 22, reagent holder 23, cuvette holder 24, and measuring unit 25.

The dispenser 26 is movable in lateral and forward-and-back directions, and can be raised and lowered. The dispenser 26 is provided with a gripper (not shown in the drawing) for gripping the cuvette, and the gripper is movable while gripping the cuvette within the cuvette holder 24. The measuring unit 25 has a plurality of holes for inserting cuvettes, and the cuvette gripped by the gripper of the dispenser 26 is inserted in a hole.

The dispenser 26 aspirates sample (plasma) and reagent, and dispenses them to the cuvettes inserted in the holes of the measuring unit 25. The measuring unit 25 is provided with a heater which heats the sample and reagent dispensed into the cuvette to a fixed temperature.

A light emitter and a light receiver (not shown in the drawing) are disposed near each hole of the measuring unit 25. The light from the light emitter irradiates the sample to which the reagent has been added, and the scattered light and light transmitted through the sample are received by the light receiver. The cover 21 has light shielding properties, such that, by closing the cover 21, external chaotic light does no influence the measurement. The reception data from the light receiver are analyzed by the control unit 6 to obtain measurement results related to blood coagulation.

The sample analyzer 1 can set one or a plurality of measurement items, such as PT (prothrombin time), APTT (activated partial thromboplastin time) and the like via user operations. The sample analyzer 1 measures the sample for the set measurement items, and displays the measurement results on the display 3. Similarly, the user may also input the reagent information (liquid information). The reagent information can be input by two methods: code reading and direct input. The reagent information is obtained when the hand-held reader 9 reads the reagent information recorded by the two-dimensional code 160 by the user scanning the two-dimensional code 160 affixed to the reagent container 150 using the hand-held reader 9. The reagent information may also be input from the reagent information input screen (described later; refer to FIGS. 8, 10, and 11) via input from a virtual keyboard on the touch panel 4.

Figure 3:
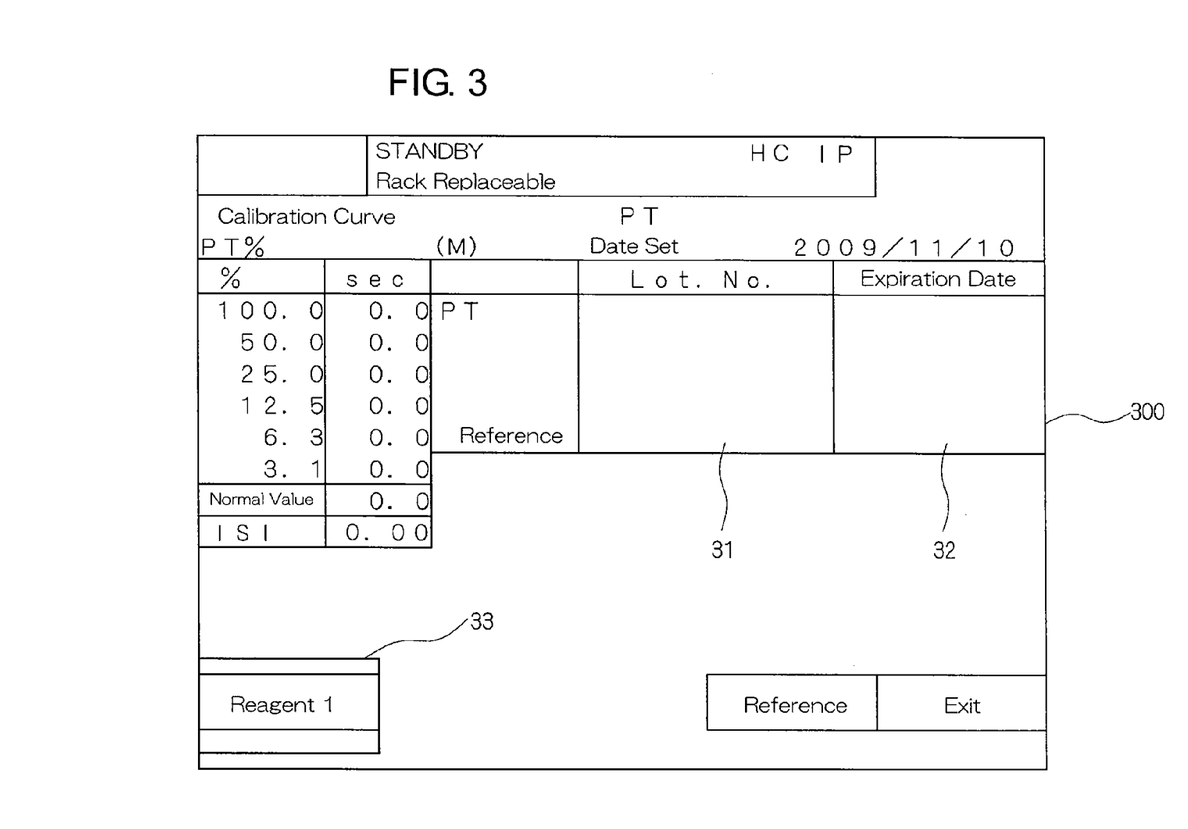
FIG. 3 shows an example of the reagent information screen of the embodiment of the sample analyzer of the present invention.

FIG. 3 shows an example of the reagent information screen of the embodiment of the sample analyzer 1 of the present invention. The reagent information screen 300 displays the lot number and expiration date of the PT reagent set in the sample analyzer 1. The lot number of the PT reagent is displayed in the lot number display field 31. The expiration date of the PT reagent is displayed in the PT reagent expiration date display field 32. Note that the condition prior to setting the PT reagent is shown in FIG. 3, so that the lot number display field 31 and the expiration date display field 32 are blank. When reagent information screen (to be described later) is displayed (refer to FIGS. 8, 10, and 11), the lot number and the expiration date are input by scanning the two-dimensional code 160 affixed to the reagent container 150 using the hand-held code reader 9, or directly inputting the information via the touch panel 4. The user calls up the reagent information screen (refer to FIGS. 8, 10, and 11) by selecting the [Reagent 1] button 33 in FIG. 3. When the selection of the [Reagent 1] button 33 is received, the CPU 61 of the control unit 6 displays the reagent information input screen (refer to FIGS. 8, 10, and 11) on the display 3 so that the input of the lot number and expiration date can be received. When the selection of the [Reagent 1] button 33 has been received, the control unit 6 detects that the condition that the reagent information (liquid information) is readable by the hand-held code reader 9.

Figure 4:
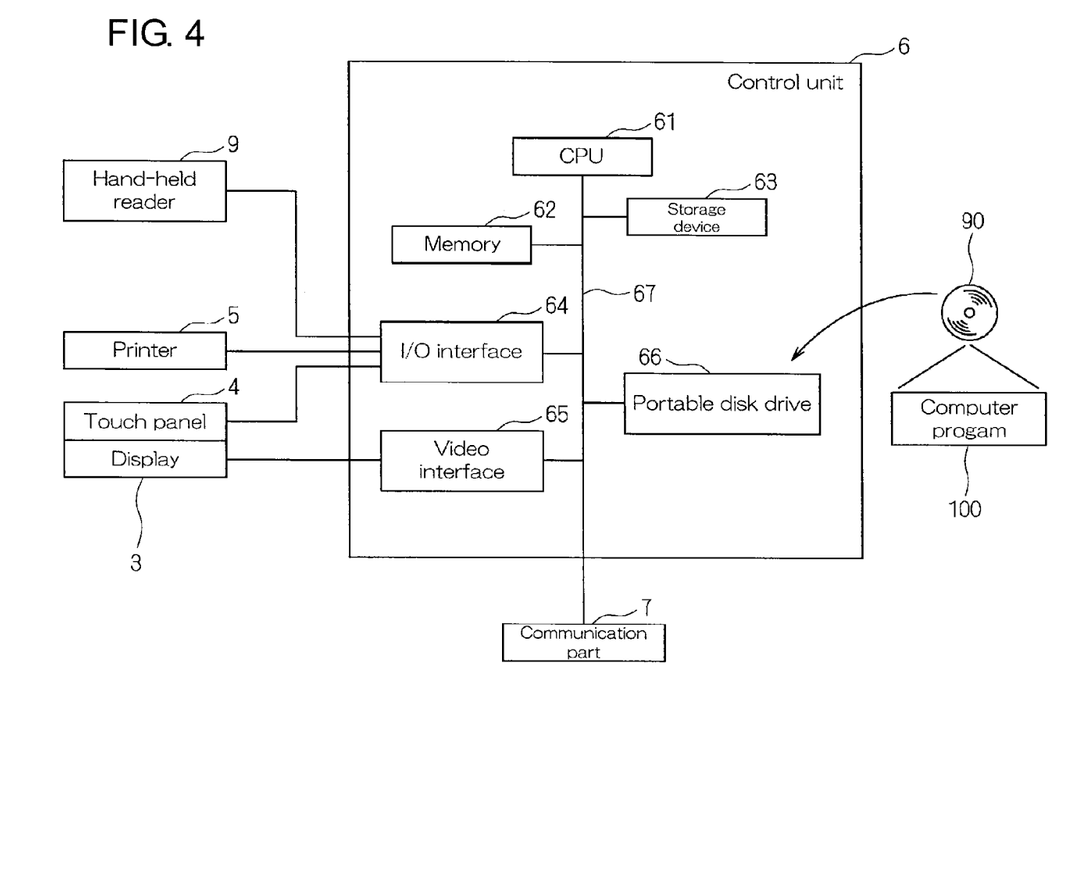
FIG. 4 is a block diagram showing the structure of the control unit of the embodiment of the sample analyzer of the present invention.

FIG. 4 is a block diagram showing the structure of the control unit 6 of the embodiment of the sample analyzer 1 of the present invention. The control unit 6 of the sample analyzer 1 is configured to use an arithmetic processing unit such as a CPU, that is, the control unit 6 is configured by, at least, a CPU (central processing unit) 61, memory 62, storage device 63, I/O interface 64, video interface 65, portable disk drive 66, and internal bus 67 connecting all such hardware. The CPU 61 is connected to each piece of hardware of the control unit 6 via the internal bus 67, and controls the operation of each piece of hardware and controls the operation of the sample analyzer 1 according to a computer program 100 stored in the storage device 63.

The memory 62 is a volatile memory such as an SRAM, flash memory, or the like, and is used to develop loaded modules when executing the computer program 100, and store temporary data generated during the execution of the computer program 100.

The storage device 63 is a an internal ROM or read/write fixed type storage device (hard disk) or the like. The computer program 100 stored in the storage device 63 is downloaded from a portable recording medium 90 such as a DVD, CD-ROM or the like which contains the recorded program and information such as data, and during execution the computer program 100 is expanded from the storage device 63 to the memory 62 and executed. Of course, the computer program 100 stored in the storage device 63 also may be a computer program downloaded from an external computer via the communication part 7.

The I/O interface 64 is connected to the touch panel 4, hand-held code reader 9, and a printer 5. The video interface 65 is connected to the display 3, which is an LCD or the like.

Figure 5:
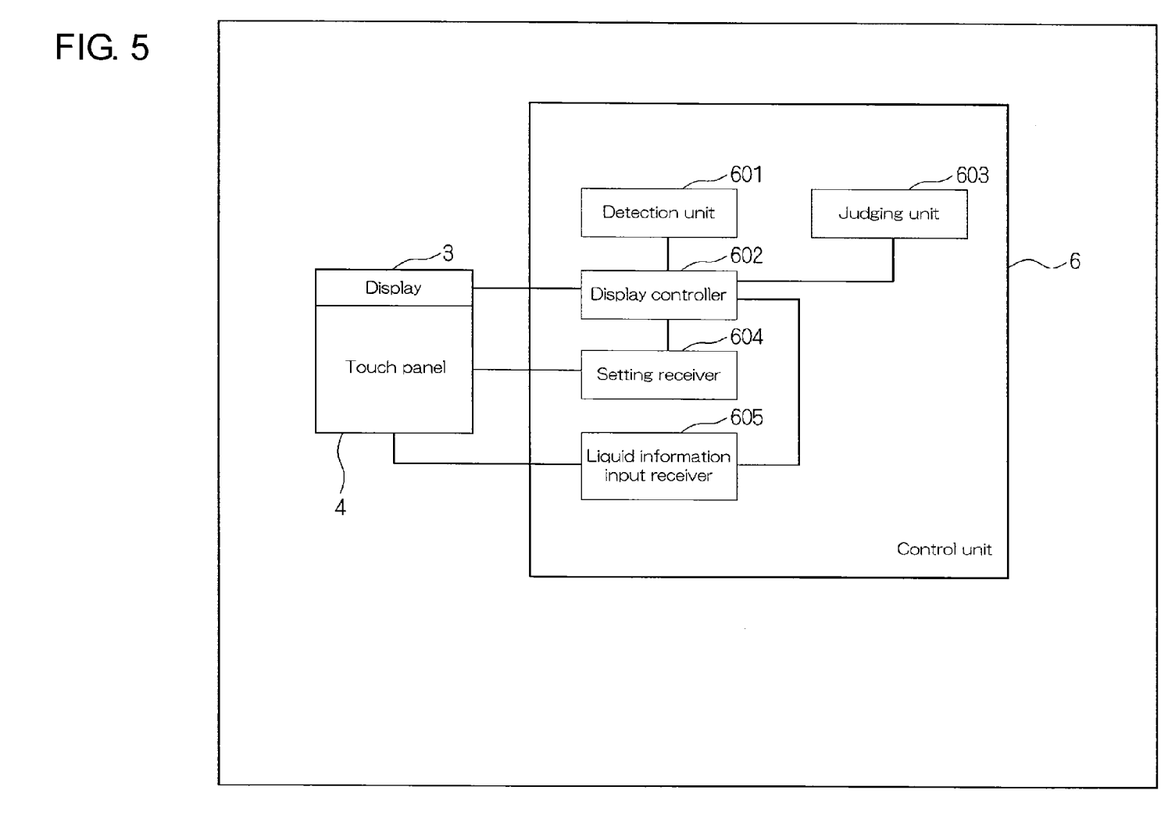
FIG. 5 is a function block diagram of the control unit of the embodiment of the sample analyzer of the present invention.

FIG. 5 is a function block diagram of the control unit 6 of the embodiment of the sample analyzer 1 of the present invention. A detection unit 601 detects the fact that the hand-held code reader 9 (reader) is ready to read the reagent information (liquid information) related to the reagent which is recorded on the two-dimensional code 160 (recording medium). Specifically, the detection unit 601 detects the fact that the selection of the [Reagent 1] button 33 has been received from the reagent information screen 300 shown in FIG. 3. At this time, the connection condition of the hand-held code reader 9 is normal, and when the reading program starts normally, a display controller 602 (to be described later) displays, on the display 3, information indicating the fact that the reagent information related to the reagent recorded by the two-dimensional code 160 can be read. That is, although the reagent information is in a readable state, the hand-held code reader 9 does not necessarily read the reagent information from the two-dimensional code 160; rather, reading of the reagent information from the two-dimensional code 160 can be performed during any part of the period during which the reagent information is readable.

During part or the entire period wherein the detection unit 601 detects that the reagent information is readable, the display controller 602 displays information indicating that the reagent information (liquid information) related to the reagent recorded on the two-dimensional code (recording medium) 160 can be read by the hand-held code reader 9. It is desirable, for example, that predetermined pattern information (icon) imitating the hand-held code reader 9 is displayed as the information indicating the fact that the reagent information related to the reagent recorded on the two-dimensional code 160 can be read by the hand-held code reader 9. The display field may be reduced since the information can be confirmed with a glance.

A judging unit 603 for determining whether the connection condition of the hand-held code reader 9 is normal during part or the entirety of the period during which the detection unit 601 detects the fact that the reagent information is readable. The icon display changes according to whether or not the connection condition is normal. When the judging unit 603 has determined that the connection condition of the hand-held code reader 9 is normal, the display controller 602 displays on the display 3 information indicating the fact that the reagent information related to the reagent recorded on the two-dimensional code 160 can be read by the hand-held code reader 9.

When the judging unit 603 has determined that the connection condition of the hand-held code reader 9 is not normal, the display controller 602 displays on the display 3 information indicating the fact that the reagent information related to the reagent recorded on the two-dimensional code 160 cannot be read by the hand-held code reader 9.

A setting receiver 604 receives settings specifying that the hand-held code reader 9 is connected or unconnected. When the setting that the hand-held code reader 9 is "connected" has been received during part or the entirety of the period during which the detection unit 601 detects the fact that the reagent information is readable, the display controller 602 displays on the display 3 information indicating the fact that the reagent information related to the reagent recorded on the two-dimensional code 160 is readable by the hand-held code reader 9.

Figure 6:
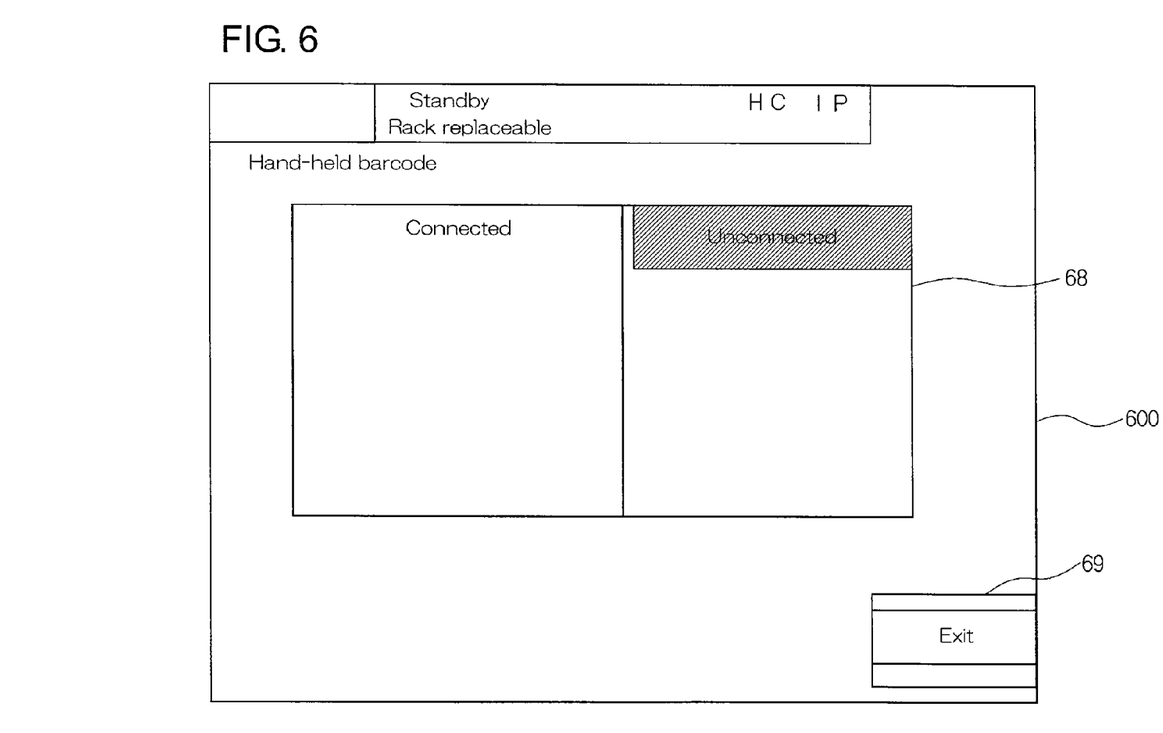
FIG. 6 shows an example of the setting screen for the hand-held code reader of the embodiment of the sample analyzer of the present invention.

FIG. 6 shows an example of the setting screen for the hand-held code reader 9 of the embodiment of the sample analyzer 1 of the present invention. As shown in FIG. 6, the [Connected] icon and the [Unconnected] icon are displayed in the setting selection field 68 of the setting screen 600. The user selects either the [Connected] icon or the [Unconnected] icon, then selects the [Exit] button 69 to set the connection condition of the hand-held code reader 9.

Returning now to FIG. 5, a liquid information input receiver 605 receives the input reagent information (liquid information) related to the reagent.

Note that, when the reagent information actually has been read in the period during which the detection unit 601 detects that the reagent information is readable, it is preferable that the display controller 602 does not display on the display 3 the information indicating the fact that the reagent information related to the reagent recorded on the two-dimensional code 160 can be read by the hand-held code reader 9. This cessation of the indication display readily confirms that the reading of the reagent information is completed and that reading is no longer necessary.

Figure 7:
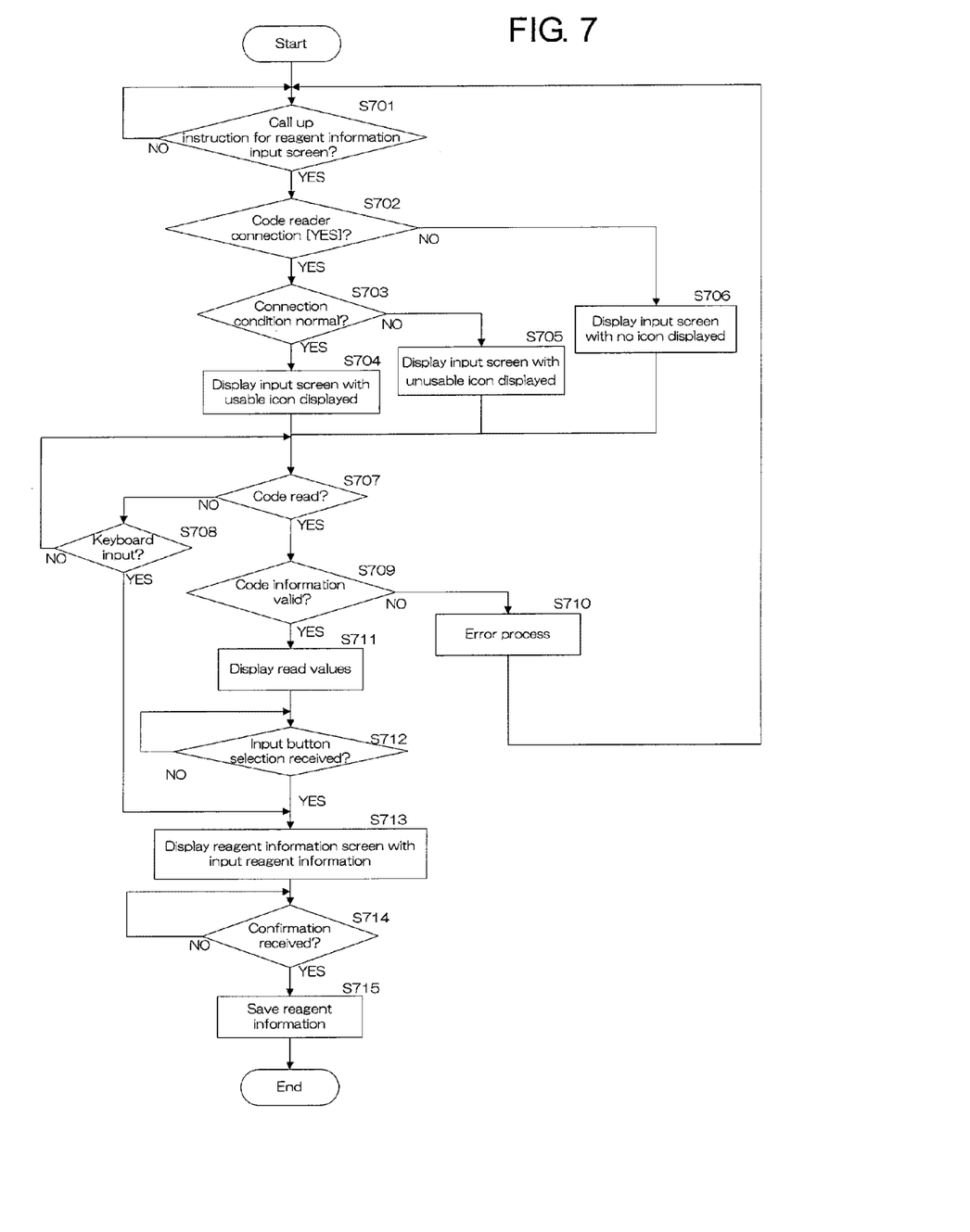
FIG. 7 is a flow chart showing the CPU processing sequence of the control unit when reagent information is input to the embodiment of the sample analyzer of the present invention.

FIG. 7 is a flow chart showing the CPU 61 processing sequence of the control unit 6 when reagent information is input to the embodiment of the sample analyzer 1 of the present invention. In FIG. 7, the CPU 61 of the control unit 6 determines whether a reagent information input screen call up instruction has been received (step S701). Specifically, the CPU 61 determines whether the selection of the [Reagent 1] button 33 has been received from the reagent information screen 300 shown in FIG. 3. When the CPU 61 determines that a call up instruction for the reagent information input screen has not been received (step S701: NO), the CPU 61 enters the standby state awaiting the reception of the call up instruction.

When the CPU 61 has determined that a call up instruction for the reagent information input screen has been received (step S701: YES), the CPU 61 then determines whether the hand-held code reader 9 connection is set to [YES] in the setting receiver 604 (step S702). When the CPU 61 has determined that the hand-held code reader 9 connection is set to [YES] (step S702: YES), the CPU 61 then determines whether the connection condition of the hand-held code reader 9 is normal (step S703). Whether or not the connection condition is normal is determined based on whether the connection line 8 is physically connected, the communication software has been started, and data communication is enabled to the controller 6 for the normally read data.

When the CPU 61 has determined that the connection of the hand-held code reader 9 is normal (step S703: YES), the CPU 61 then displays the reagent information input screen 800 (refer to FIG. 8) which displays the usable icon as information indicating that the reagent information related to the reagent recorded on the two-dimensional code 160 is readable by the hand-held code reader 9 (step S704).

Figure 8:
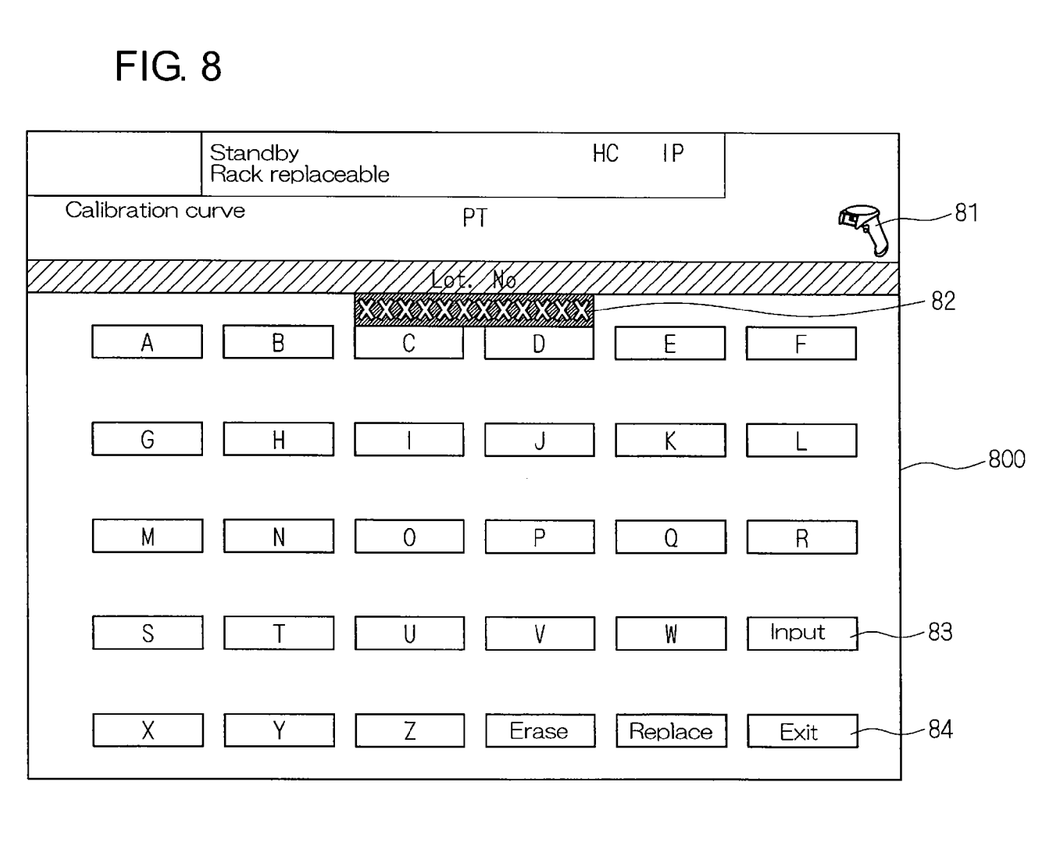
FIG. 8 shows an example of the reagent information input screen indicating the usable icon of the embodiment of the sample analyzer of the present invention.

FIG. 8 shows an example of the reagent information input screen 800 which displays the usable icon of the embodiment of the sample analyzer 1 of the present invention. The example of FIG. 8 shows a screen for receiving the input of the reagent lot number as the reagent information (liquid information).

When the connection condition of the hand-held code reader 9 is normal, a usable icon imitating the hand-held code reader 9 is displayed at the upper right of the reagent information input screen 800. The reagent lot number received by direct input is displayed in the lot number display field 82. In FIG. 8, the lot number display field 82 is blank because the lot number has not been input yet. When inputting other reagent information related to the reagent, for example, the expiration date, the selection of the [Input] button 83 is received to transition the screen to the reagent information input screen allowing reception of a sequence of other reagent information. When the user obtains reagent information using the hand-held code reader 9 while the reagent information input screen 800 is being displayed, the screen transitions to the reading confirmation screen 900 (refer to FIG. 9) for confirming the content of the read reagent information.

Figure 9:
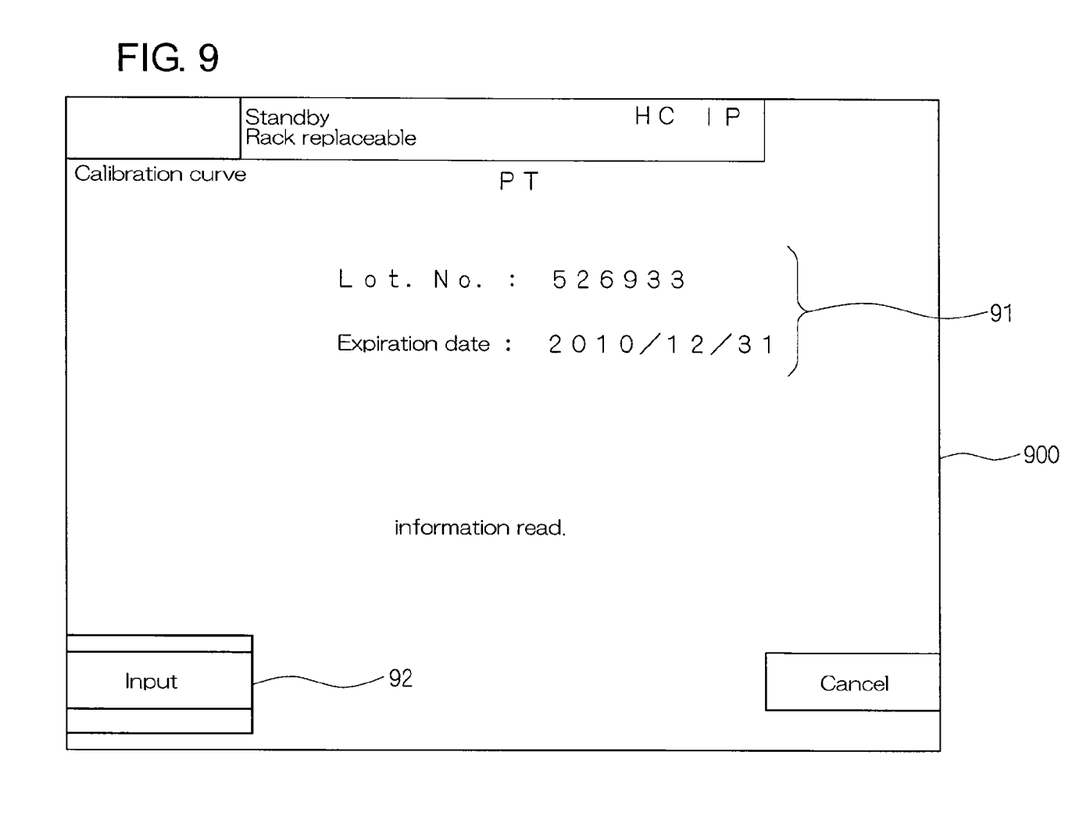
FIG. 9 shows an example of the reading confirmation screen of the embodiment of the sample analyzer of the present invention.

FIG. 9 shows an example of the reading confirmation screen 900 of the embodiment of the sample analyzer 1 of the present invention. In FIG. 9, the lot number and the expiration date are read as reagent information. In FIG. 9, examples of the read values of the read lot number and expiration date are displayed in the read value display field 91. The user selects the [Input] button 92 when the user has confirmed the displayed lot number and expiration date and decided that a normal reading was completed. The CPU 61 of the control unit 6 displays the reagent information screen 1200 (refer to FIG. 12) with the input reagent information when the selection of the [Input] button 92 has been received.

The usable icon 81 displayed in the reagent information input screen 800 is not displayed in FIG. 9. That is, when the reagent information has been read using the hand-held code reader 9 while the reagent information input screen of FIG. 800 is being displayed, the screen transitions to the reading confirmation screen 900 of FIG. 9 and the usable icon 81 is erased. In the present embodiment, the reagent information can be read using the hand-held code reader 9 only when the reagent information input screen 800 of FIG. 8 is being displayed, whereas the reagent information cannot be read using the hand-held code reader 9 at the stage wherein the screen has transitioned to the reading confirmation screen 900 of FIG. 9. The user can readily see that the reagent information cannot be read from the two-dimensional code 160 by confirming that the screen has transitioned to the reading confirmation screen 900 of FIG. 9 in which the usable icon 81 is not displayed.

Returning now to FIG. 7, when the CPU 61 has determined that the connection of the hand-held code reader 9 is abnormal (step S703: NO), the CPU 61 then displays the reagent information input screen 1000 (refer to FIG. 10) which displays an unusable icon as the information indicating that the reagent information related to the reagent recorded on the two-dimensional code 160 is unreadable by the hand-held code reader 9 (step S705).

Figure 10:
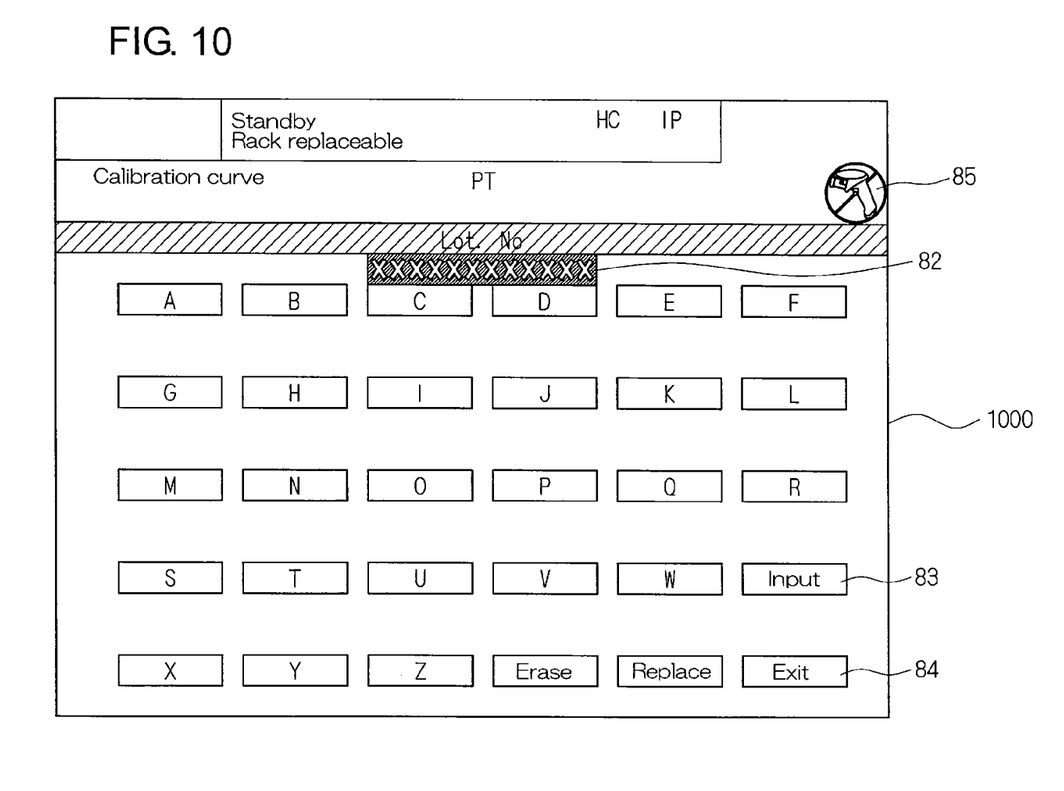
FIG. 10 shows an example of the reagent information input screen displaying the usable icon of the embodiment of the sample analyzer of the present invention.

FIG. 10 shows an example of the reagent information input screen 1000 which displays the unusable icon of the embodiment of the sample analyzer 1 of the present invention. As shown in FIG. 10, the screen is identical to that of FIG. 8 with the exception that the unusable icon 85 is displayed in the upper right of the screen. In the condition shown in FIG. 10, the user cannot read the reagent information related to the reagent recorded by the two-dimensional code 160 using the hand-held code reader 9. In this case, therefore, the user directly inputs the reagent information via the touch panel 4. After the reagent information has been input, the user selects the [Exit] button 84. The CPU 61 of the control unit 6 displays the reagent information screen 1200 (refer to FIG. 12) with the input reagent information when the selection of the [Exit] button 84 has been received.

Returning now to FIG. 7, when the CPU 61 of the control unit 6 has determined that the connection of the hand-held code reader 9 is not set to [YES] (step S702: NO), the CPU 61 displays the reagent information input screen 1100 (refer to FIG. 11) without the icon display (step S706).

Figure 11:
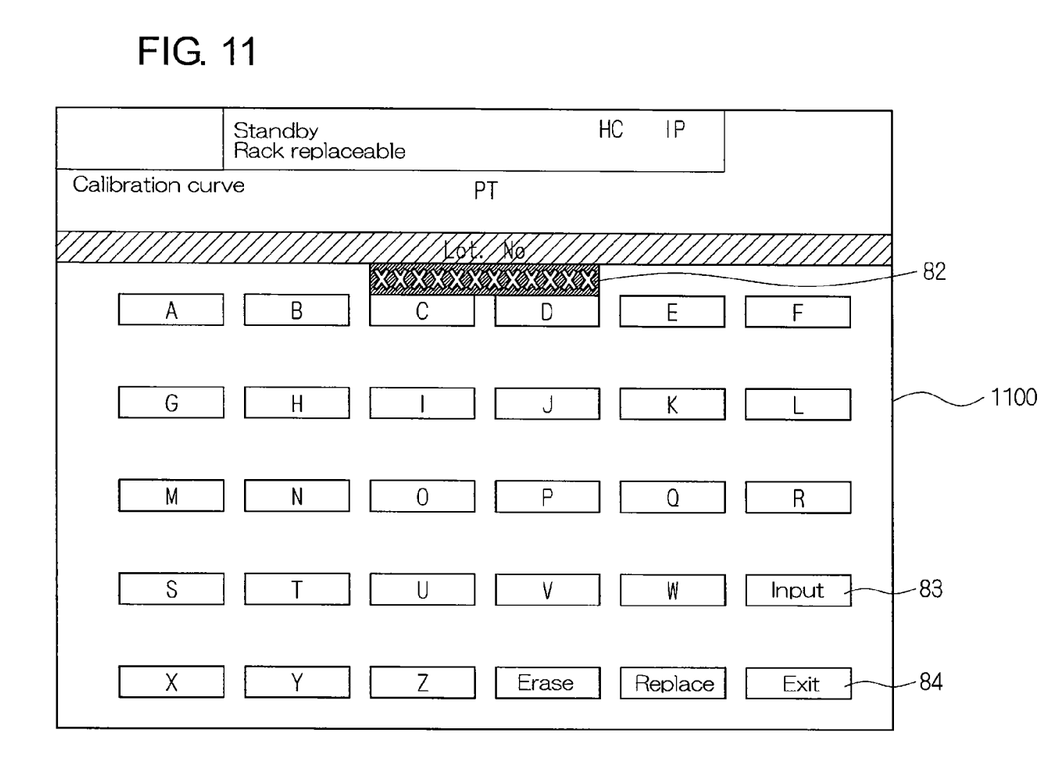
FIG. 11 shows an example of the reagent information input screen without the icon display of the embodiment of the sample analyzer of the present invention.

FIG. 11 shows an example of the reagent information input screen 1100 without the icon display of the embodiment of the sample analyzer 1 of the present invention. As shown in FIG. 11, the screen is identical to that of FIGS. 8 and 10 with the exception that the icon is not displayed in the upper right area of the screen. In the condition shown in FIG. 11, the user cannot read the reagent information related to the reagent recorded by the two-dimensional code 160 using the hand-held code reader 9. In this case, therefore, the user directly inputs the reagent information via the touch panel 4. After the reagent information has been input, the user selects the [Exit] button 84. The CPU 61 of the control unit 6 displays the reagent information screen 1200 (refer to FIG. 12) with the input reagent information when the selection of the [Exit] button 84 has been received.

Returning again to FIG. 7, the CPU 61 of the control unit 6 determines whether the input of the reagent information via code reading has been received (step S707). When the CPU 61 has determined that the input of the reagent information has not been received by the code reading (step S707: NO), the CPU 61 then determines whether the input of the reagent information has been received via direct input from the virtual keyboard of the touch panel 4 (step S708). Whether the direct input has been received is determined based on whether the lot number has been input from the virtual keyboard of the touch panel 4 and the selection of the [Exit] button 84 has been received.

When the CPU 61 has determined that direct input from the keyboard has been received (step S708: YES), the display 3 displays the reagent information screen with the input reagent information (refer to FIG. 12) (step S713). When the CPU 61 has determined that direct input of the reagent information has not been received (S708: NO), the CPU 61 returns the process to step S707 and the process described above is repeated. When the CPU 61 has determined that input by code reading has been received (step S707: YES), the CPU 61 then determines whether the input reagent information is valid (step S709). The CPU 61 determines whether the read information is valid as code information based on, for example, a check digit.

When the CPU 61 has determined that the reagent information read by the hand-held code reader 9 is invalid (step S709: NO), the CPU 61 executes an error process (step S710), returns the process to step S710, and repeats the above described process. When the CPU 61 has determined that the read code information is valid (step S709: YES), the CPU 61 displays the reading confirmation screen 900 of FIG. 9 on the display 3 (step S711). The CPU 61 determines whether the selection of the input button 92 has been received (step S712). When the CPU 61 has determined that the selection of the input button 92 has not been received (step S712: NO), the CPU 61 enters the standby state and awaits the reception of the input button 92 selection. When the CPU 61 has determined that the selection of the input button 92 has been received (step S712: YES), the CPU 61 displays the reagent information screen 1200 (refer to FIG. 12) with the input reagent information on the display 3 (step S713), and determines whether confirmation has been received indicating to save the received reagent information (step S714).

Figure 12:
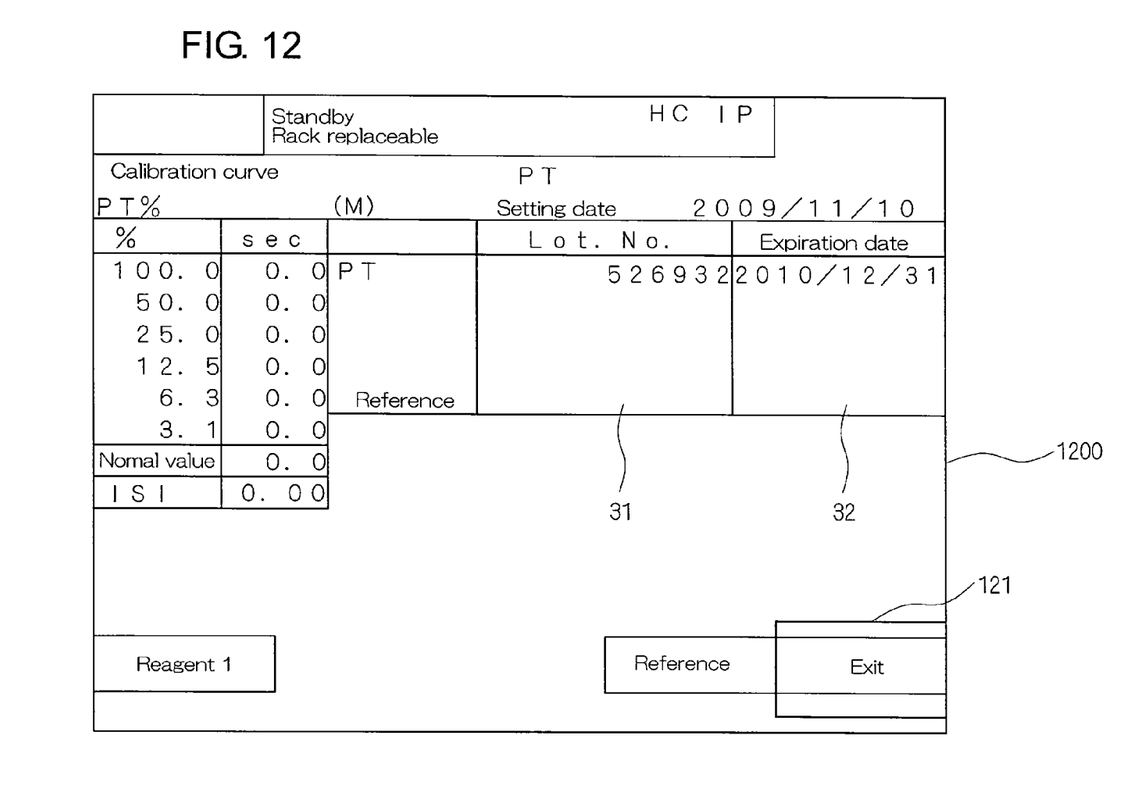
FIG. 12 shows an example of the reagent information screen with input reagent information of the embodiment of the sample analyzer of the present invention.
Figure 13:
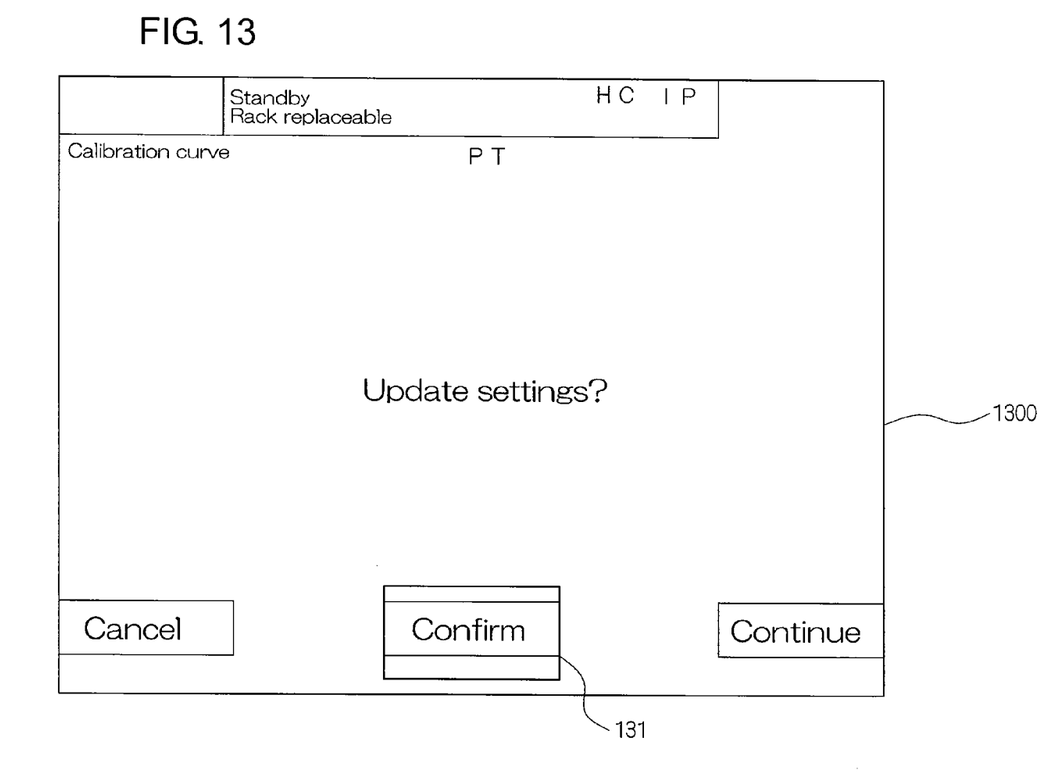
FIG. 13 shows an example of a confirmation screen for confirming whether to save the input reagent information of the embodiment of the sample analyzer of the present invention.

FIG. 12 shows an example of the reagent information screen with input reagent information of the embodiment of the sample analyzer 1 of the present invention, and FIG. 13 shows an example of a confirmation screen for confirming whether to save the input reagent information of the embodiment of the sample analyzer 1 of the present invention. A lot number and expiration date are displayed for each reagent in the reagent information screen 1200 shown in FIG. 12, and the user selects the [Exit] button 121 after confirming the content is error free. When the selection of the [Exit] button 121 has been received, the CPU 61 of the control unit 6 displays the confirmation screen 1300 shown in FIG. 13. In FIG. 13, the input reagent information is saved in the storage device 63 and the reagent information is updated via the reception of the selection of the [Confirmation] button 131.

Returning to FIG. 7, when the CPU 61 of the control unit 6 has determined that confirmation has not been received (step S714: N), the CPU 61 enters the standby state and awaits confirmation reception. When the CPU 61 has determined that confirmation has been received (step S714: YES), the CPU 61 stores the input reagent information in the storage device 63 (step S715).

According to the embodiment described above, the user can readily comprehend the timing by which reagent information is readable by confirming that the information indicating that reagent information is readable via the hand-held code reader 9 is displayed on the display 3.

Note that although the reagent information is read by scanning the two-dimensional code 160 affixed to the reagent container 150 as a recording medium in the present embodiment, the type of recording medium is not specifically limited inasmuch as either a unidimensional barcode may be used as well as a two-dimensional code. The recording medium is also not specifically limited to optical reading inasmuch as reading via magnetism, radio wave and the like also may be used, for example RFID.

Although the above embodiment describes a mode of reading reagent information recorded by a two-dimensional code 160 affixed to the reagent container 150 via a hand-held code reader 9, the present invention is not limited to this mode. For example, the recording medium may be affixed to paper provided separately from the liquid container. In this case, the user reads the liquid information from the recording medium affixed to the paper using a reader, places the liquid container corresponding to the read liquid information into the sample analyzer, and executes sample analysis.

Although the above embodiment describes a hand-held type reader which is used while the user holds the reader in his/her hand, the present invention is not limited to this mode. For example, the reader also may be installed in the sample analyzer so that the liquid information is read by scanning the recording medium via the installed reader while the user holds the recording medium in his/her hand.

Note that the present invention is not limited to the above embodiment, inasmuch as substitutions and a wide range of modifications are possible within the scope of the claims. For example, although a determination is made as to whether the input of the lot number and expiration date have been received, that is whether selection of the [Reagent 1] button 33 has been received in the above embodiment, reception of the input of the lot number and expiration date also may be detected, for example, by the sample analyzer 1 detecting that a reagent container 150 is empty.

A further embodiment involves a code which includes the reagent information being downloaded over the Internet to an information terminal such as a personal computer, smart phone or the like, and saved therein, so that the stored code can be printed on paper which is then read. Alternatively, the downloaded and saved code may be displayed on a display, such that the reagent information recorded in memory can be obtained by reading the displayed two-dimensional code.

What is claimed is:

1. A sample analyzer for analyzing a sample by using a liquid in a container, comprising:
   a reader that reads information of a liquid in a container, the information of the liquid being stored in a storage medium;
   a display;
   a controller including a processor and a memory under control of the processor;
   a measuring unit configured to perform sample measurements comprising a plurality of holes;
   a light emitter and a light receiver disposed near each of the plurality of holes, the light emitter configured to irradiate the sample with light thereby producing at least one of scattered light and light transmitted through the sample, the light receiver configured to receive at least one of the scattered light and the light transmitted through the sample and produce reception data, wherein the controller is configured to analyze the reception data to obtain a measurement result; and
   an interface configured to be connected to the reader and to relay between the controller and the connected reader,
   wherein the memory is configured to store instruction causing the processor to carry out operations comprising:
   displaying a reagent information screen including a button for receiving the instruction of displaying the input screen;
   receiving the instruction of displaying an input screen for receiving information of a liquid via the reader when the button is pressed, wherein the input screen includes a symbol of the reader on the display to indicate the reader is connected;
   reading the information of the liquid container; and
   in response to a reading of the information of the liquid container by the connected reader while the input screen is displayed, displaying a confirmation screen instead of the input screen on the display, wherein the confirmation screen includes the information of the liquid container read by the connected reader and does not include the symbol of the reader;
   wherein the reagent information screen does not include the symbol of the reader.

2. The sample analyzer of claim 1, further comprising an input device, wherein the controller causes the display to display the confirmation screen when the information of the liquid has been inputted by the input device.

3. The sample analyzer of claim 1, wherein the confirmation screen further includes an information stating that an instruction to store the read information into the memory is acceptable, and in response to the instruction to store, the controller stores the read information into the memory.

4. The sample analyzer of claim 3, wherein the display comprises a touch panel, the input screen includes a button for receiving the instruction to store, and when the button is pressed on the touch panel, the controller stores the read information in the memory.

5. The sample analyzer of claim 1, wherein the symbol comprises an image that imitates the reader.

6. The sample analyzer of claim 1, wherein the reader is a reader of the hand-held type.

7. The sample analyzer of claim 6, wherein the information of liquid comprises the lot number of the reagent.

8. The sample analyzer of claim 6, wherein the information of the liquid comprises the expiration of the reagent.

9. The sample analyzer of claim 1, wherein the reader is an optical reader.

10. The sample analyzer of claim 1, wherein a code is adhered to the outside of a container.

11. The sample analyzer of claim 1, wherein a code is printed to a label attached to a container.

12. The sample analyzer of claim 1, wherein the liquid is a reagent used in the analyzer.

13. The sample analyzer of claim 1, wherein the sample analyzer is an apparatus for analyzing blood coagulation.

14. The sample analyzer of claim 1, wherein the confirmation screen includes a lot number of the liquid as the read information.

15. The sample analyzer of claim 1, wherein the confirmation screen includes an expiration date of the liquid as the read information.

16. The sample analyzer of claim 1, wherein the input screen includes keys to input information of liquid.

* * * * *